United States Patent [19]

Yagita et al.

[11] Patent Number: 4,650,672
[45] Date of Patent: Mar. 17, 1987

[54] MULTI-COLORED PRESSED COSMETIC POWDER AND METHOD OF PREPARING SAME

[75] Inventors: Yoshiaki Yagita; Yutaka Okunuki, both of Sagamihara; Toshihide Ikeda, Urayasu; Shoji Hyodo, Machida, all of Japan

[73] Assignee: Shiseido Co., Ltd., Tokyo, Japan

[21] Appl. No.: 527,824

[22] Filed: Aug. 30, 1983

[30] Foreign Application Priority Data

Sep. 11, 1982 [JP] Japan ................... 57-158703

[51] Int. Cl.$^4$ .................... A61K 7/035; A61K 7/021
[52] U.S. Cl. ........................ 424/69; 424/63; 514/844
[58] Field of Search ............... 424/63, 64, 69; 106/308 F, 291, 300, 305, 308 B; 514/844

[56] References Cited

U.S. PATENT DOCUMENTS

| | | | |
|---|---|---|---|
| 3,479,429 | 11/1969 | Morshauser et al. | 424/63 |
| 3,615,809 | 10/1971 | Nagle et al. | 106/300 |
| 4,170,487 | 10/1979 | Robertson et al. | 106/309 |
| 4,390,524 | 6/1983 | Nasuno et al. | 424/63 |

FOREIGN PATENT DOCUMENTS

| | | | |
|---|---|---|---|
| 1467730 | 2/1969 | Fed. Rep. of Germany | 424/63 |
| 1064713 | 5/1954 | France . | |
| 2248023 | 5/1975 | France . | |
| 19663 | 5/1974 | Japan . | |
| 58-24510 | 2/1983 | Japan | 424/63 |
| 1486634 | 9/1977 | United Kingdom . | |

OTHER PUBLICATIONS

Balsam et al., Cosmetics: Science and Technology, 2nd ed., Wiley, N.Y.
Soap, Perfumery and Cosmetics, vol. 50, No. 9, Sep. 1977, pp. 365-370, Londres, GB, "Eye Make-Up Formulations", p. 366.
Soap, Perfumery and Cosmetics, vol. 43, No. 7, Jul. 1970, pp. 425-426, Londres, GB, "Lustre Pigments in Eye Make-Up and Lipstick".

Primary Examiner—Sam Rosen
Assistant Examiner—Shawn P. Foley
Attorney, Agent, or Firm—Parkhurst & Oliff

[57] ABSTRACT

A cosmetic suitable for application to the skin (such as eye-shadow, rouge and pressed face powder) is formed by mixing differently colored pigment compositions with binders to form differently colored grains, intermixing the grains and compression-moulding them into a compact, but without destroying the grain structure thereof. The differently colored grains may then separately or simultaneously be applied to the skin with a puff.

16 Claims, 4 Drawing Figures

MULTI-COLORED PRESSED COSMETIC POWDER AND METHOD OF PREPARING SAME

BACKGROUND OF THE INVENTION

The present invention concerns cosmetics to be applied on the skin such as eye shadow, rouge and pressed face powder, and the method for preparing the same. In the prior art, this type of cosmetics consisted of just a single color, and they were defective in that the make-up using them tended to become monotonous. Even though one may use a plural number of cosmetics of different colors, there appeared distinct borders between colors which have been overlayed. It was therefore impossible to achieve a free make-up with subtle combinations of colors.

SUMMARY OF THE INVENTION

The present invention aims at offering a novel cosmetic free of all the defects as above described, and the method of preparing the same. The cosmetic according to the present invention, in sum, combines bases using different color pigments, and so that these different color bases can be mixed simultaneously or separately with a puff or a chip to facilitate application of the same on the skin. The method of preparing such a cosmetic, in sum, comprises using as a first base composition pigment in powder form or a granular pigment solidified by a binder and a second base composition with a pigment having a color which is different from the pigment used for the first base, said bases being formed into grains by a binder, and compress-moulding the bases without destroying their respective granular forms.

The details, characteristics, advantages, etc. of the cosmetic according to the present invention and the method of preparing the same will become clearer from the appended drawings and the description given below in respect of embodiments thereof.

BRIEF EXPLANATION OF THE DRAWINGS

The drawings illustrate embodiments of the present invention wherein.

DETAILED EXPLANATION OF THE PREFERRED EMBODIMENTS

The present invention concerns an utterly new and novel cosmetic free of all the defects as above described, and offers a cosmetic using a first base A of suitable pigment either in powdered form or in grains, and a second base B consisting of a pigment which has a color different from the first base A and which is formed into grains by a binder, mixing these bases while keeping the grains intact and concurrently compress-moulding the same. This cosmetic, therefore, will have a random pattern with different colors in its cross section in an arbitrary direction passing through its center. This cosmetic further comprises a blocks consisting of a first powdered pigment base intermixed with blocks consisting of a powdered pigment base having a color different from that of the first powdered pigment base, said differently colored blocks being closely and integrally coupled to each other. Such a combination of powdered pigment blocks illustrated in FIG. 1, wherein the base 1 and the differently colored base 2 are shown in the prescribed blocks within a container 3 such as a compact. The user transfers the single color of the base 1 or the base 2 to the face by a puff or the like, just as in the conventional method of applying cosmetics. If the puff is slidably moved from the base 2 to the base 1, then it will have plural colors thereon. When the puff is slidably moved at right angles to the border of the base 2 and the base 1, the puff will have the colors in layers. If the puff is slidably moved along the border of the base 2 and the base 1, the two colors are relatively independently transferred onto the puff.

Figure 1:
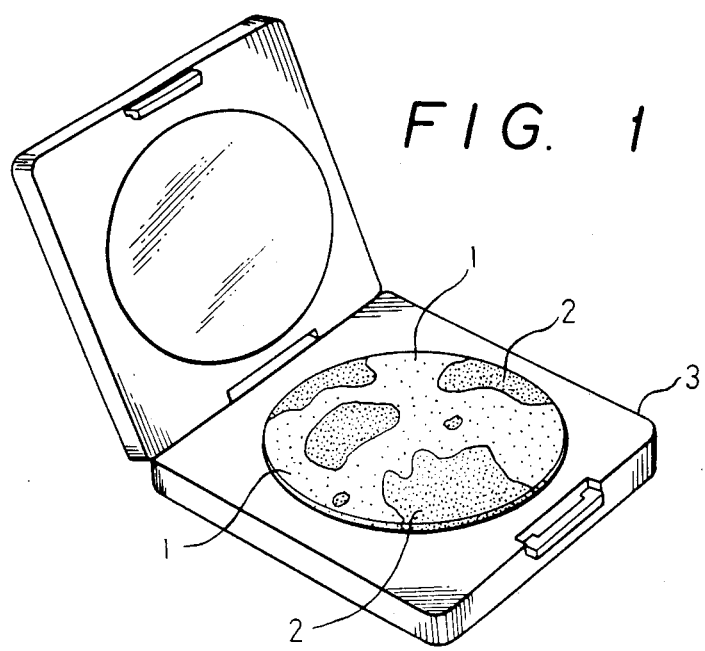
FIG. 1 is a perspective view of the cosmetic as filled inside a container.
Figure 2:
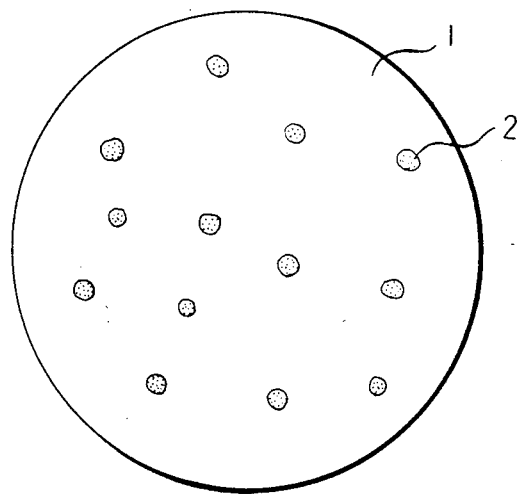
FIGS. 2 to 4 show plane views of cosmetics embodying the present invention.

In the embodiment shown in FIG. 1, the base 1 and the base 2 were rather roughly separated, but as shown in another embodiment in FIG. 2, the quantity of the base 2 may be decreased compared to the base 1, and the base 2 may be formed into small grains. It naturally is possible, too, to reverse the quantitative relationship between the bases 1 and 2. This embodiment is more suitable than the embodiment of FIG. 1 for transferring more than one color relatively independently of each other.

Figure 3:
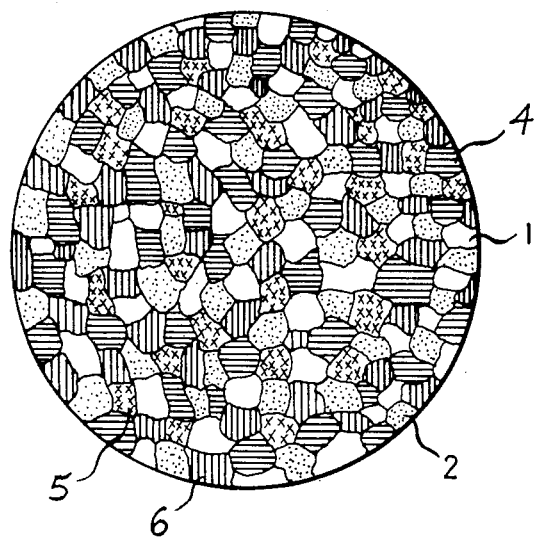

In still another embodiment shown in FIG. 3, the bases 2 and 1 are further differentiated with the base 2 having several different colors resulting in several differently colored blocks 1, 2, 4, 5, 6. This embodiment is more suitable than the embodiment of FIG. 1 for transferring multiple colors in a mixed state. Thus, it is possible to apply a make up combining fancy colors by freely adjusting the sliding motion of the puff over the mosaic of the blocks 1, 2, 4, 5, 6, according to the individual's preferences.

Figure 4:
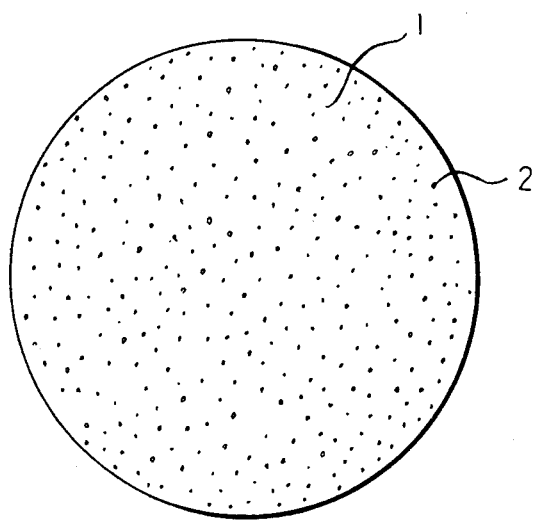

In yet another embodiment of the present invention which is shown in FIG. 4, the base 2 is formed in blocks even smaller than those in the embodiment of FIG. 2, and are dispersed in a comparatively uniform manner throughout the base 1. In this embodiment, the colors of the bases 2 and 1 are highly mixed, and yet the base 2 having a color different from that of the base 1 is dispersed throughout the transferred cosmetic, thereby enabling expression of subtle changes in colors.

When the bases 1 and 2 are used in grain form, the grain diameter is adjusted to a range from 0.02-5 mm$\phi$, and more preferably from 0.2-2.5 mm$\phi$. If the grain size of the bases 1 and 2 are increased, then controlling the sliding motion of the puff will beter allow the user to obtain pure colors. If, on the other hand, the grain size of the base 2 is decreased, then it is possible to obtain subtle color changes as the base 2 of a different color from that of the base 1 is present in the transferred cosmetic.

The bases 1 and 2 consist generally of the same materials, but they are different in that the pigment colors are different and that base 2 is formed into grains by a binder, while the base 1 may be in either the powdered form or granular form. The materials used for the bases (so called "extenders") are talc, kaolin, mica and titanium dioxide, while the materials used for the pigment are red, yellow and black iron oxide, ultramarine, blue, green, etc., prussian blue and other chronium type pigments, organic pigments (such as color index constitution number [hereinafter "C.I."] 73360, C.I. 74160, C.I. 11680) and others. In order to enhance the finishing effect of the make-up, fish scales as a natural pearl-like substance, titanium dioxide coated mica type synthetic pearl-like pigment, titanium dioxide coated mica colored with carmine, titanium dioxide coated mica colored with metal oxide type pearl-like pigments and, titanium dioxide coated mica colored with prussian blue may be added.

Binders to convert the bases consisting of the above mentioned materials into grains may be oil, caulking agent, water, alcohol, volatile solvents, etc. Oil materials, aliphatic and aromatic esters or ethers which are used as cosmetic ingredients may also be added. For example, liquid paraffin and squalane etc. are used as hydrocarbon oil, isopropyl myristate, monoglyceride as mono-esters, glycol derivatives and diglyceride as di-esters, trimethyl propane derivatives and triglyceride as tri-esters and pentaerythritol derivatives etc. As caulking agents such water soluble polymers as gelatine and casein derived from natural animals and starch, arabic gum, guar gum, locust been gum, tragacanth gum derived from plants are used. Starch derivatives (processed starch), cellulose derivatives (methylcellulose), etc. and polyvinyl alcohol, polyvinyl pyrrolidone, etc. are also used. Montmorillonite group clay minerals such as sodium magnesium silicate and magnesium aluminium silicate are also used.

Depending on the purpose for which the product is intended, various additives such as antiseptics, suitable pharmaceutical agents, perfumes, surfactants, antioxidants, chelating agents, ultraviolet absorption agents, etc., may be added arbitrarily.

There are various ways of forming the bases into grains using the materials as above mentioned; one is to mix a suitable amount of oil as a binder with the base and obtain a clay-like substance and then form the obtained substance into grains using a grain moulding machine or an extruder/moulder. Another method mixes a suitable amount of deionized water or hydrated alcohol as a binder with the base 1 or 2 to obtain a clay-like substance, which is then formed into grains by a grain moulding machine or an extruder/moulder. Still another method mixes a suitable amount of a caulking agent or of deionized water or hydrated alcohol as a binder with bases to obtain a clay-like substance, and form the same into grains by a grain moulding machine or an extruder/moulder. The term grain as used herein does not specify the size of a mass, but describes a state where the particles in powder form are bound together in a mass by a binder, thereby achieving the purpose of the present invention. They may be discrete and small in size as shown in FIG. 3 or a larger clay-like mass so long as they achieve the purpose of the present invention. The shape thereof may be chosen arbitrarily.

When forming the above mentioned bases into grains, the grain diameter should be 0.02–5 mmφ or preferably 0.2–2.5 mmφ. If the diameter is less than 0.02 mmφ, it is impossible to create different colors in the transferred portion, whereas if it is over 5 mmφ, it is not possible to effeciently arrange the bases of different colors inside a compact. Therefore, the optimum size is within the range of 0.20 mm–2.5 mmφ.

Thus obtained granular bases or the powdered base 1 and granular base 2 (which have different colors from each other) are filled and compressed inside the inner plate of a cosmetic container or a mould while keeping the grain form intact. What is meant by the phrase "keeping the grain form intact" is not necessarily to completely retain the grain form obtained by said grain moulding machine, but to retain the borders of the bases formed into block forms during compression moulding, and to keep the grain forms to such a degree that a plurality of colors may be separately transferrable by a puff, a chip, etc. It further is possible to obtain complex color variations by using bases of more than two colors. If deionized water or hydrated alcohol is used as a binder, then it is necessary to dry the compression-formed substance for several tens of minutes at 37°–80° C. in order to let the binder vaporize.

The details of the present invention are now explained in further detail by way of examples.

EXAMPLE 1

|  | Eye-shadow | (in wt. %) |
|---|---|---|
| Base A | mica | 34.00 |
|  | talc | 20.00 |
|  | TiO2—mica | 19.80 |
|  | ultramarine green | 20.00 |
|  | squalane | 5.00 |
|  | sorbitan sesquioleate | 1.00 |
|  | antiseptic | 0.05 |
|  | antioxidant | 0.05 |
|  | perfume | 0.10 |
| Base B | mica | 29.00 |
|  | talc | 20.00 |
|  | TiO2—mica | 19.80 |
|  | C.I.73360 | 10.00 |
|  | squalane | 20.00 |
|  | sorbitan sesquioleate | 1.00 |
|  | antiseptic | 0.05 |
|  | antioxidant | 0.05 |
|  | perfume | 0.10 |

The base A in a powder form is mixed with the base B moulded into grains at the ratio of 95 wt%: 5 wt% to be compressed inside a container while keeping the grains intact.

EXAMPLE 2

|  | Eye-shadow | (in wt. %) |
|---|---|---|
| Base A | mica | 17.30 |
|  | fish scale | 25.00 |
|  | iron oxide, yellow | 1.50 |
|  | ultramarine blue | 5.00 |
|  | sodium magnesium silicate | 1.00 |
|  | antiseptic | 0.05 |
|  | antioxidant | 0.05 |
|  | perfume | 0.10 |

The above ingredients are uniformly mixed, added with 50 wt% of ion exchange water, keaded and then formed into grains by a grain moulding machine.

| Base B | mica | 16.50 |
|---|---|---|
|  | fish scale | 24.80 |
|  | iron oxide, red | 7.50 |
|  | sodium magnesium silicate | 1.00 |
|  | antiseptic | 0.05 |
|  | antioxidant | 0.05 |
|  | perfume | 0.10 |

The above ingredients are uniformly mixed, added with 50 wt% of deionized water, kneaded and then formed into grains by a grain moulding machine.

To 90 wt% of the above base A formed into grains, 10 wt% of the base B is added and the resultant mixture is placed in the container without damaging the grains, compression moulded and dried for 30 minutes at 50° C.

EXAMPLE 3

| | rouge | (in wt. %) |
|---|---|---|
| Base A | mica | 39.00 |
| | talc | 29.80 |
| | TiO$_2$—mica + carmine | 20.00 |
| | C.I. 11680 | 5.00 |
| | isopropyl myristate | 6.00 |
| | antiseptic | 0.05 |
| | antioxidant | 0.05 |
| | perfume | 0.10 |
| Base B | mica | 21.80 |
| | talc | 15.00 |
| | TiO$_2$—mica + Fe$_2$O$_3$ | 10.00 |
| | sodium magnesium silicate | 1.00 |
| | C.I. 73360 | 2.00 |
| | antiseptic | 0.05 |
| | antioxidant | 0.05 |
| | perfume | 0.10 |

The above ingredients are uniformly mixed, added with 50 wt% deionized water, kneaded and then formed into grains using a grain moulding machine.

| | | |
|---|---|---|
| Base B' | mica | 17.30 |
| | fish scales | 25.00 |
| | iron oxide, yellow | 1.50 |
| | ultramarine blue | 5.00 |
| | sodium magnesium silicate | 1.00 |
| | antiseptic | 0.05 |
| | antioxidant | 0.05 |
| | perfume | 0.10 |

The above ingredients are mixed uniformly, added with 50 wt% deionized water, kneaded and then formed into grains using a grain moulding machine.

To 70 wt% of the above powder base A, 15 wt% each of the base B and the base B' are added, and the resultant mixture is filled inside a container while keeping the grains intact, compressed and dried at 37° C. for 60 minutes.

EXAMPLE 4

| | rouge | (in wt. %) |
|---|---|---|
| Base A | talc | 43.80 |
| | TiO$_2$—mica + prussian blue | 30.00 |
| | iron oxide, red | 5.00 |
| | iron oxide, yellow | 10.00 |
| | squalane | 5.00 |
| | magnesium stearate | 5.00 |
| | sorbitan sesquioleate | 1.00 |
| | antiseptic | 0.05 |
| | antioxidant | 0.05 |
| | perfume | 0.10 |
| Base B | talc | 25.80 |
| | TiO$_2$—mica + Prussian blue | 15.00 |
| | C.I. 73360 | 1.00 |
| | iron oxide, yellow | 2.50 |
| | squalane | 2.50 |
| | magnesium stearate | 2.50 |
| | sorbitan sesquioleate | 0.50 |
| | antiseptic | 0.05 |
| | antioxidant | 0.05 |
| | perfume | 0.10 |

The above ingredients for base B are uniformly mixed, added with 50 wt% of deionized water as a binder, kneaded and then formed into grains using a grain moulding machine.

The base A in the above ingredients is in powder form, while the base B is in a grain form. To 50 wt% of the former is added 50 wt% of the base B formed in grains, and the resultant mixture is filled in a container while keeping the grains intact, compressed and dried at 45° C. for 30 minutes.

EXAMPLE 5

| | Pressed face powder | (in wt. %) |
|---|---|---|
| Base A | kaolin | 10.00 |
| | mica | 20.00 |
| | titanium dioxide | 15.00 |
| | iron oxide, red | 3.00 |
| | iron oxide, yellow | 5.00 |
| | iron oxide, black | 0.50 |
| | liquid paraffin | 35.05 |
| | glyceril monoisostearate | 5.00 |
| | polyethelene wax | 5.00 |
| | sorbitan monooleate | 1.00 |
| | antiseptic | 0.20 |
| | antioxidant | 0.05 |
| | perfume | 0.20 |
| Base B | talc | 15.55 |
| | kaolin | 10.00 |
| | mica | 20.00 |
| | titanium dioxide | 20.00 |
| | iron oxide, red | 5.00 |
| | iron oxide, yellow | 7.00 |
| | iron oxide, black | 1.00 |
| | liquid paraffin | 15.00 |
| | glyceril monooleate | 5.00 |
| | sorbitan sesquiisostearate | 1.00 |
| | antiseptic | 0.20 |
| | antioxidant | 0.05 |
| | perfume | 0.20 |

The above ingredients for the base B are uniformly mixed and then formed into grains using a grain moulding machine. The base A is formed into clay-like grains, to 80 wt% of which is added 20 wt% of the base B, and the resultant mixture is filled in a container keeping the grains intact, and compressed.

EXAMPLES 6 TO 10

For these examples 6 to 10, the compositions, the ratio of the base A and B, and the method of preparing as for examples 1 to 5 were employed, except that the grain diameters for the base A and B were set as follows.

| Examples | Composition, ratio of bases, and preparing method | Grain formed base A and/or base B (mm$\phi$) | |
|---|---|---|---|
| | | Base A | Base B |
| 6 | The same as Example 1 | — | 1–2 |
| 7 | The same as Example 2 | 4–5 | 0.25–1.17 |
| 8 | The same as Example 3 | — | Base B 0.02–0.25, Base B' 2–3 |
| 9 | The same as Example 4 | — | 3–4 |
| 10 | The same as Example 5 | 1–2 | 1–2 |

What we claim is:

1. A cosmetic comprising a first powdered pigment composition and a second powdered pigment composition formed into grains using a binder, said second composition having a color different from that of the first composition, the first composition and the second composition being heterogeneously intermixed and compression-moulded together while keeping the grain form of the second composition intact and the differently colored pigments separate from one another.

2. The cosmetic as claimed in claim 1 wherein the grain diameter of the grains of the second composition is 0.02–5 mm.

3. The cosmetic as claimed in claim 1 wherein the first and second compositions are intermixed in such a way that a cross-section in an arbitrary direction passing through the center of the cosmetic formed thereof always presents random patterns of different colors.

4. The cosmetic as claimed in claim 2 wherein the two compositions are intermixed in such a way that a cross-section in an arbitrary direction passing through the center of the cosmetic formed thereof always presents random patterns of different colors.

5. A method of preparing a cosmetic comprising placing a first powdered pigment composition and a second powdered pigment composition formed into grains using a binder, said second composition having a color different from that of the first composition, into a container heterogeneously intermixing the compositions and compression-moulding the compositions together while keeping the grain form of the second composition intact and the differently colored pigments separate from one another.

6. The method of preparing a cosmetic as claimed in claim 5 wherein the grain diameter of the grains of the second composition is from 0.02 to 5 mm.

7. A cosmetic comprising a first powdered pigment composition formed into grains using a binder and a second powdered pigment composition formed into grains using a binder, said second composition having a color different from that of the first composition, the first composition and the second composition being heterogeneously intermixed and compression-moulded together while keeping the grain forms thereof intact and the differently colored pigments separate from one another.

8. The cosmetic as claimed in claim 7 wherein the grain diameter of the grains of at least one of the compositions is 0.02–5 mm.

9. The cosmetic as claimed in claim 7 wherein the first and second compositions are intermixed in such a way that a cross-section in an arbitrary direction passing through the center of the cosmetic formed thereof always presents random patterns of different colors.

10. The cosmetic as claimed in claim 8 wherein the first and second compositions are intermixed in such a way that a cross-section in an arbitrary direction passing through the center of the cosmetic formed thereof always presents random patterns of different colors.

11. A method of preparing a cosmetic comprising placing a first powdered pigment composition formed into grains using a binder and a second powdered pigment composition formed into grains using a binder, said second composition having a color different from that of the first composition, into a container heterogeneously intermixing the compositions and compression-moulding the compositions together while keeping the grain forms thereof intact and the differently colored pigments separate from one another.

12. The method of preparing a cosmetic as claimed in claim 11 wherein the grain diameter of the grains of at least one of the compositions is 0.02–5 mm.

13. The cosmetic as claimed in claim 1, wherein the first and second powdered pigment compositions further comprise cosmetics selected from the group consisting of eye-shadow, rouge and pressed face powder.

14. The cosmetic as claimed in claim 7, wherein the first and second powdered pigment compositions further comprise cosmetics selected from the group consisting of eyeshadow, rouge and pressed face powder.

15. A method as claimed in claim 5, wherein the first and second powdered pigment compositions further comprise cosmetics selected from the group consisting of eyeshadow, rouge and pressed face powder.

16. A method as claimed in claim 11, wherein the first and second powdered pigment compositions further comprise cosmetics selected from the group consisting of eye-shadow, rouge and pressed face powder.

* * * * *

UNITED STATES PATENT AND TRADEMARK OFFICE
CERTIFICATE OF CORRECTION

PATENT NO. : 4,650,672
DATED : March 17, 1987
INVENTOR(S) : YAGITA et al.

It is certified that error appears in the above-identified patent and that said Letters Patent is hereby corrected as shown below:

Column 1, line 27, after "composition" insert --a--.

Column 1, line 61, delete "a" (first occurrence).

Column 1, line 67, after "blocks" insert --is--.

Column 2, line 23, after "differentiated" insert --,--.

Column 2, line 24, after "colors" insert --,--.

Column 2, line 25, after "blocks" insert --,--.

Column 2, line 46, change "beter" to --better--.

Column 2, line 68, after "pigments" insert --,--.

Column 2, line 68, after "and" delete ",".

Column 3, line 7, change "." to --,--.

Column 3, line 7, change "For" to --for--.

UNITED STATES PATENT AND TRADEMARK OFFICE
CERTIFICATE OF CORRECTION

PATENT NO. : 4,650,672
DATED : March 17, 1987
INVENTOR(S) : Yagita et al

It is certified that error appears in the above-identified patent and that said Letters Patent is hereby corrected as shown below:

Column 3, line 54, change "effeciently to
-- efficiently--.

Signed and Sealed this

Thirteenth Day of October, 1987

Attest:

DONALD J. QUIGG

*Attesting Officer*  *Commissioner of Patents and Trademarks*